United States Patent
Lapota et al.

(10) Patent No.: US 7,559,236 B1
(45) Date of Patent: Jul. 14, 2009

(54) PORTABLE PROFILER FOR PROFILING A MARINE BIOSPHERE AND METHOD OF ASSEMBLING THE PROFILER

(75) Inventors: David Lapota, San Diego, CA (US); Gregory Wayne Anderson, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 37 days.

(21) Appl. No.: 11/726,205

(22) Filed: Mar. 20, 2007

(51) Int. Cl.
*G01C 5/00* (2006.01)
(52) U.S. Cl. .................................................. 73/170.29
(58) Field of Classification Search ............... 73/170.29
See application file for complete search history.

(56) References Cited

U.S. PATENT DOCUMENTS

| | | | |
|---|---|---|---|
| 3,996,794 A * | 12/1976 | Helgans, Jr. ............. 73/170.29 |
| 4,446,542 A * | 5/1984 | Beckerle ..................... 367/131 |
| 5,264,906 A | 11/1993 | Ferer | |
| 5,481,904 A * | 1/1996 | Fleck et al. ................. 73/61.51 |
| 5,633,460 A * | 5/1997 | Manmaru et al. ......... 73/170.31 |
| 5,840,572 A | 11/1998 | Copeland | |
| 6,570,176 B1 | 5/2003 | Fucile | |
| 7,034,327 B2 | 4/2006 | Fucile | |

OTHER PUBLICATIONS

Laurence Lippsett, "New Instrument Sheds Light On Bioluminescence", Oceanus, Nov. 29, 2006, Woods Hole Oceanographic Institution, Woods Hole, Massachusetts.

* cited by examiner

*Primary Examiner*—Andre J Allen
(74) *Attorney, Agent, or Firm*—Kyle Eppele; Peter A. Lipovsky; J. Eric Anderson

(57) ABSTRACT

Portable profiler for profiling a marine biosphere and method of assembling the profiler. A portable profiler is provided for profiling a marine biosphere, comprising a housing; a ballast coupled to the housing for controlling movement of the housing in the biosphere; a light-sensitive detector assembly coupled to the housing for detecting bioluminescence, the detector assembly capable of generating an output signal in response to the bioluminescence detected thereby; and a data analysis and storage device coupled to the light-sensitive detector assembly for receiving the output signal.

42 Claims, 10 Drawing Sheets

US 7,559,236 B1

PORTABLE PROFILER FOR PROFILING A MARINE BIOSPHERE AND METHOD OF ASSEMBLING THE PROFILER

STATEMENT REGARDING FEDERALLY SPONSORED RESEARCH OR DEVELOPMENT

The invention claimed herein may be manufactured and used by or for the Government of the United States of America for governmental purposes without payment of any royalties thereon or therefor. This application and any patent issuing thereon is assigned to the United States Government and is available for licensing for commercial purposes. No license is necessary when used for Governmental purposes. Licensing and technical inquiries may be directed to the Office of Patent Counsel, Space and Naval Warfare Systems Center, Code 20012, San Diego, Calif., 92152.

BACKGROUND OF THE EMBODIMENTS OF THE INVENTION

The embodiments of the portable profiler and method disclosed herein generally relate to employing the phenomenon of bioluminescence for assessing the environmental characteristics of a marine environment.

For health reasons, it is desirable to test for the presence of toxins in bodies of water, such as lakes, streams, rivers and oceans. A possible technique for detecting the presence of environmental toxins in water may beneficially use the phenomenon of bioluminescence.

Bioluminescence is light generated by a chemical reaction within an organism, such as a marine organism, wherein chemical energy is converted into light energy. The chemical that produces the light is luciferin, which the organism acquires by diet or by internal synthesis. A chemical known as luciferase catalyzes the oxidation of luciferin to produce the light.

Examples of marine organisms that evince bioluminescence include dinoflagellates and zooplankton. Dinoflagellate "blooms" (i.e., population congregations so dense that they discolor the water red or brown to form so-called "red" tides) of these organisms have been observed to degrade water quality and produce toxins harmful to other marine organisms, such as seals. Such toxins can even affect humans such as by paralytic shellfish poisoning. It is known that bioluminescence diminishes in presence of toxic chemicals. However, a problem in the art is lack of a suitable device to sense bioluminescence for detecting toxins in water.

BRIEF SUMMARY OF EMBODIMENTS OF THE INVENTION

A portable profiler is provided for profiling a marine biosphere, comprising a housing; a ballast coupled to said housing for controlling movement of said housing in the biosphere; and a light-sensitive detector assembly coupled to said housing for detecting bioluminescence, said detector assembly capable of generating an output signal in response to the bioluminescence detected thereby; and a data analysis and storage device coupled to said light-sensitive detector assembly for receiving the output signal.

Also, there is provided a method of assembling a portable profiler for profiling a marine biosphere, comprising the steps of; coupling a ballast to said housing for controlling movement of said housing in the biosphere; coupling a light-sensitive detector assembly to said housing for detecting bioluminescence, said detector assembly capable of generating an output signal in response to the bioluminescence detected thereby; and coupling a data analysis and storage device to said light-sensitive detector assembly for receiving the output signal.

BRIEF DESCRIPTION OF THE SEVERAL VIEWS OF THE DRAWING(S)

While the specification concludes with claims particularly pointing-out and distinctly claiming the subject matter of the profiler and method, it is believed the subject matter of the portable profiler and method will be better understood from the following description when taken in conjunction with the accompanying drawings wherein:

DETAILED DESCRIPTION OF REPRESENTATIVE EMBODIMENT(S) OF THE INVENTION

Figure 1:
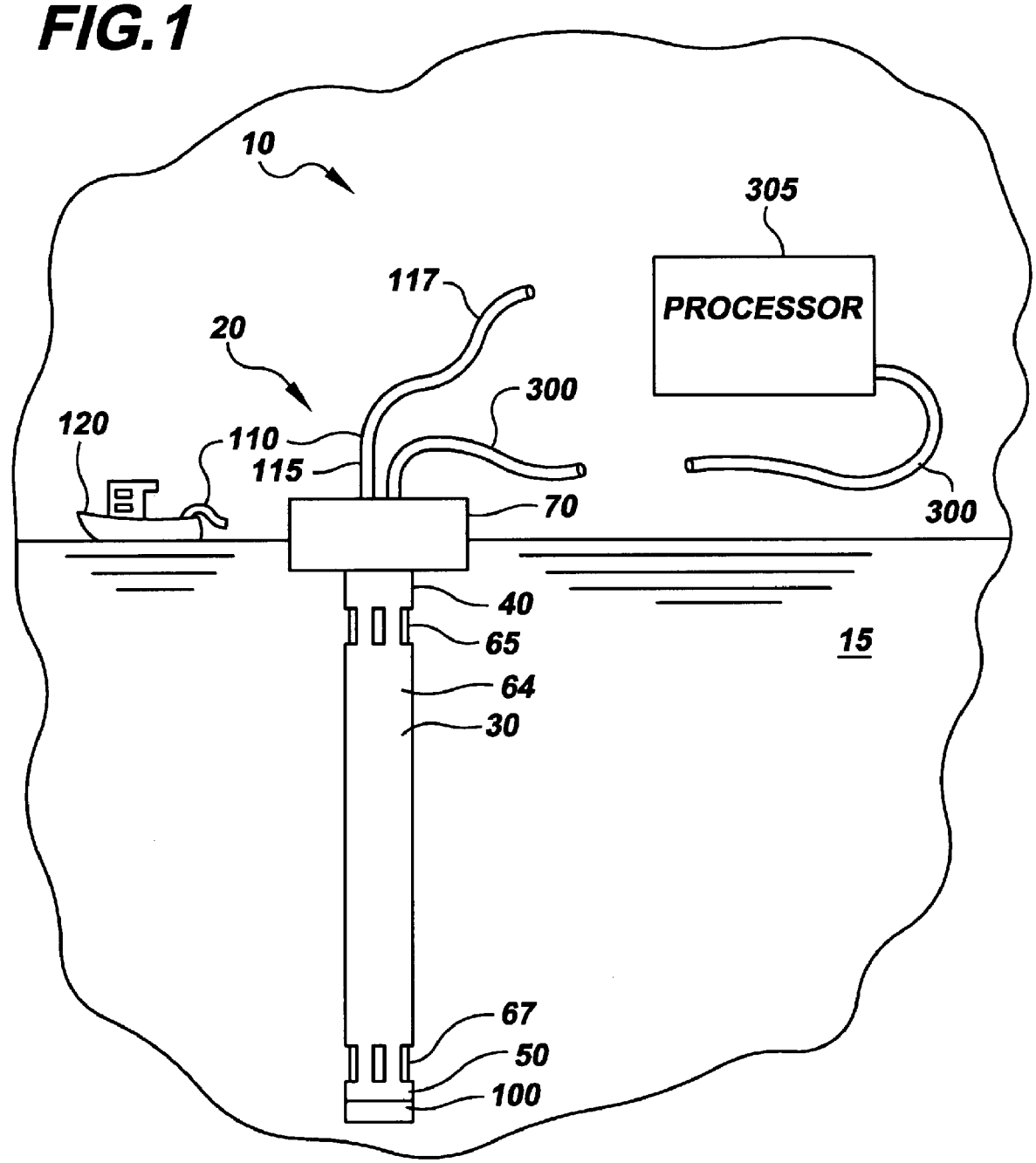
FIG. 1 is a view in elevation of a first embodiment portable profiler having a plurality of detectors disposed therein, the profiler including a processor capable of recording readings taken by the detectors.
Figure 1A:
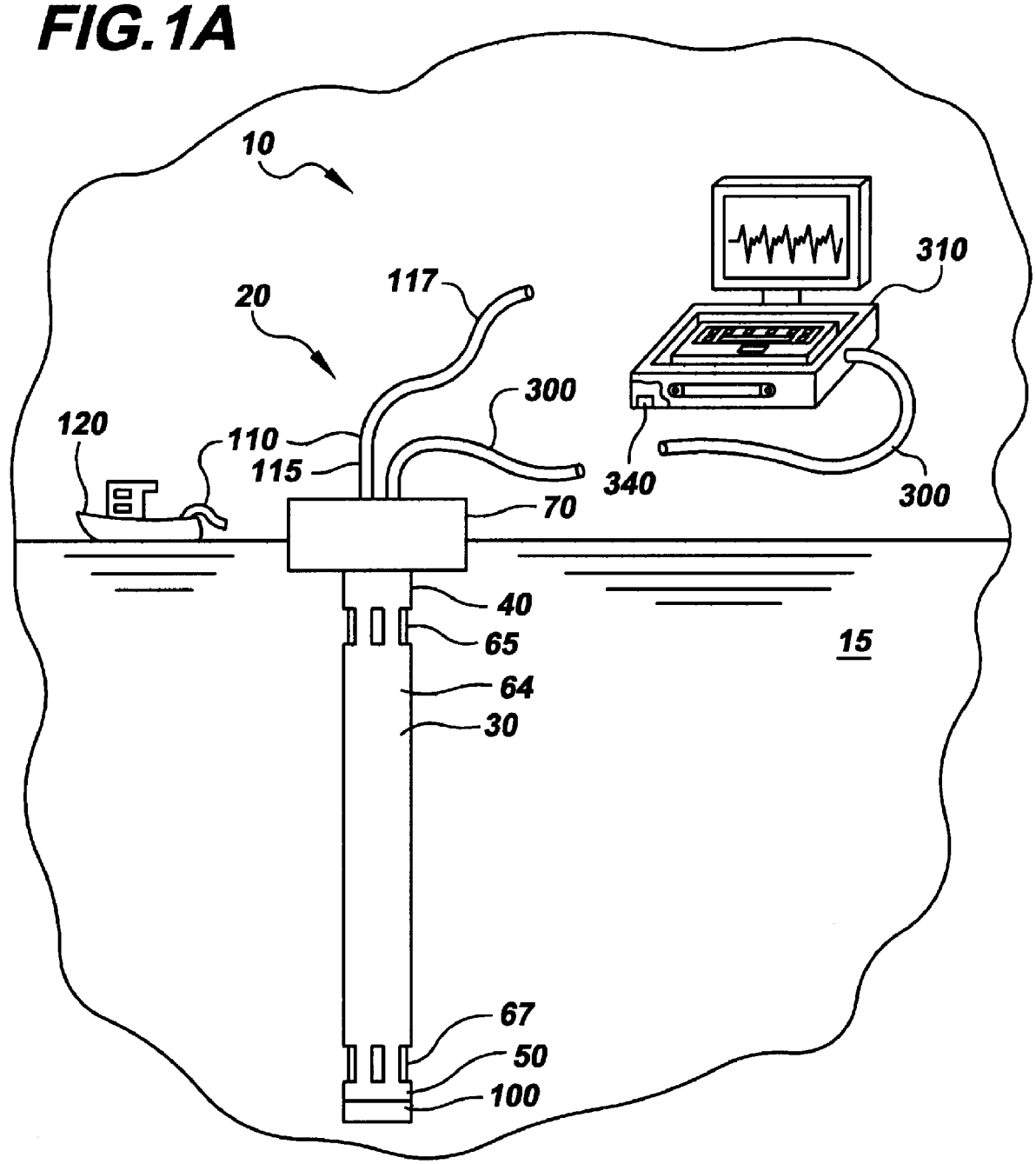
FIG. 1A is a view in elevation of the first embodiment portable profiler, an embodiment of the processor being shown as a laptop computer.

The representative embodiments of the portable profiler disclosed herein will be directed in particular to elements forming part of, or cooperating more directly with, an apparatus in accordance with the invention. It is to be understood that elements not specifically shown or described may take various forms well known to those skilled in the art.

Therefore, referring to FIGS. 1, 1A, 2 and 3, there is shown a first embodiment portable profiler, generally referred to as 10, for profiling a marine biosphere 15. Profiler 10 comprises a low-weight housing, generally referred to as 20, that includes a tubular member 30. Tubular member 30 is sized to facilitate convenient lifting and handling by a human operator of profiler 10. Tubular member 30 has a first end 40 and a second end 50. Also, tubular member 30 defines an interior 60, an inner wall 62 and an outer wall 64. For reasons described hereinbelow, formed through tubular member 30 near first end 40 is a plurality of spaced-apart intake ports 65 extending around the perimeter of tubular member 30. It may be appreciated that tubular member 30 may take any convenient shape in transverse cross-section, such as circular, square, triangular, or other shapes. In addition, for reasons described hereinbelow, formed through tubular member 30 near second end 50 are a plurality of spaced-apart outlet ports 67 extending around the perimeter of tubular member 30. Mounted, such as by welding, on first end 40 of tubular member 30 is a hollow generally disk-shaped cap 70 defining a chamber 80 therein. Formed through cap 70 are a first bore 90a and a second bore 90b for reasons described hereinbelow. Although it is contemplated that profiler 10 may be deployed in an ocean, it will be appreciated that profiler 10 may be deployed in lakes, bays or rivers, as well, to detect bioluminescent organisms therein and other characteristics (e.g., temperature) of the marine biosphere of interest.

Referring again to FIGS. 1, 1A, 2 and 3, attached to second end 50 is a ballast member 100 for stabilizing housing 20 in marine biosphere 15, which may be a body of water having wave action tending to rock profiler 10 to-and-fro. With regard to enhancing stabilization, ballast 100 lowers the center of gravity of housing 20 to improve the stabilization of housing 20, particularly when the previously mentioned to-and-fro rocking motion is pronounced. Improving stabilization may assist in obtaining more reliable or repeatable test results. Also, ballast 100 adds mass to housing 20 for causing housing 20 to descend into biosphere 15 for testing at predetermined depths in biosphere 15. Moreover, connected to cap 70 is a flexible cable 110 having a first end 115 thereof affixed in first bore 90a and a second end 117 attached to a deployment vessel 120 capable of deploying profiler 10 from a land-based staging area to a predetermined location at biosphere 15. However, profiler 10 may be deployed at biosphere 15 by alternative means, such as by a helicopter 118, as described more fully hereinbelow. Moreover, in the case of helicopter deployment, cable 110 may engage a winch mechanism 119 that is connected to helicopter 118 for lowering housing 20 into biosphere 15 and for raising housing 20 from biosphere 15. In addition, biosphere 15 may have corrosive salt content. With regard to reducing corrosive attack of biosphere 15 on profiler 10, the profiler 10 may be fabricated from a corrosion-resistant material such as aluminum, bronze, brass, stainless steel, titanium, or even a suitable ceramic or plastic.

As previously mentioned, it is desirable to detect bioluminescence. For example, bioluminescence diminishes in the presence of toxic chemicals: therefore, the phenomenon of bioluminescence may be used as indicia of water quality. Further, it is useful to conduct basic research that studies the phenomenon of bioluminescent organisms. Hence, there is a need to detect bioluminescence for reasons of environmental water quality monitoring and for the purpose of marine research.

Figure 2:
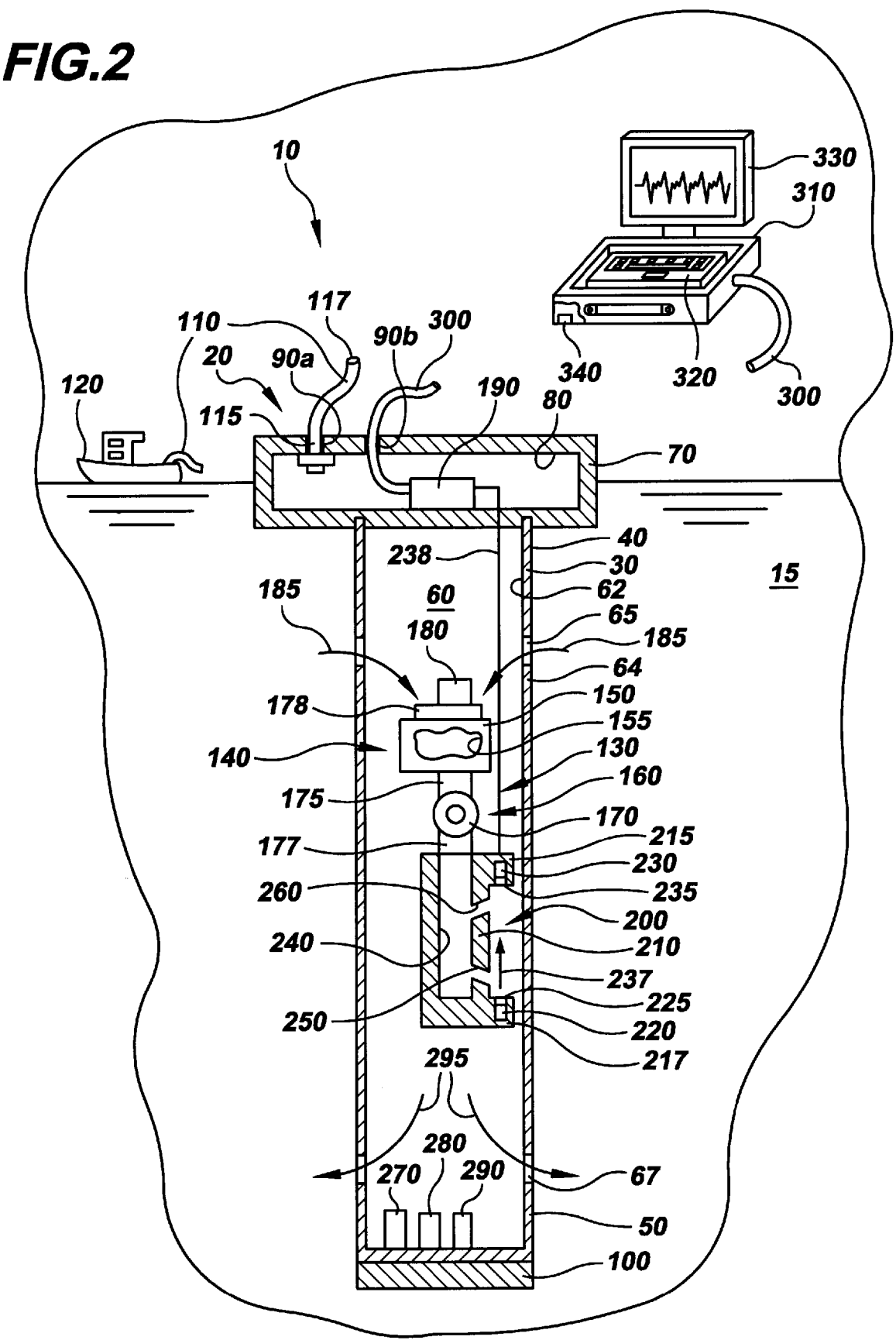
FIG. 2 is a view in partial elevation of the first embodiment portable profiler, this view showing a test assembly disposed in a tubular member belonging to the first embodiment portable profiler and also showing a deployment vessel for deploying the profiler in a marine biosphere.
Figure 3:
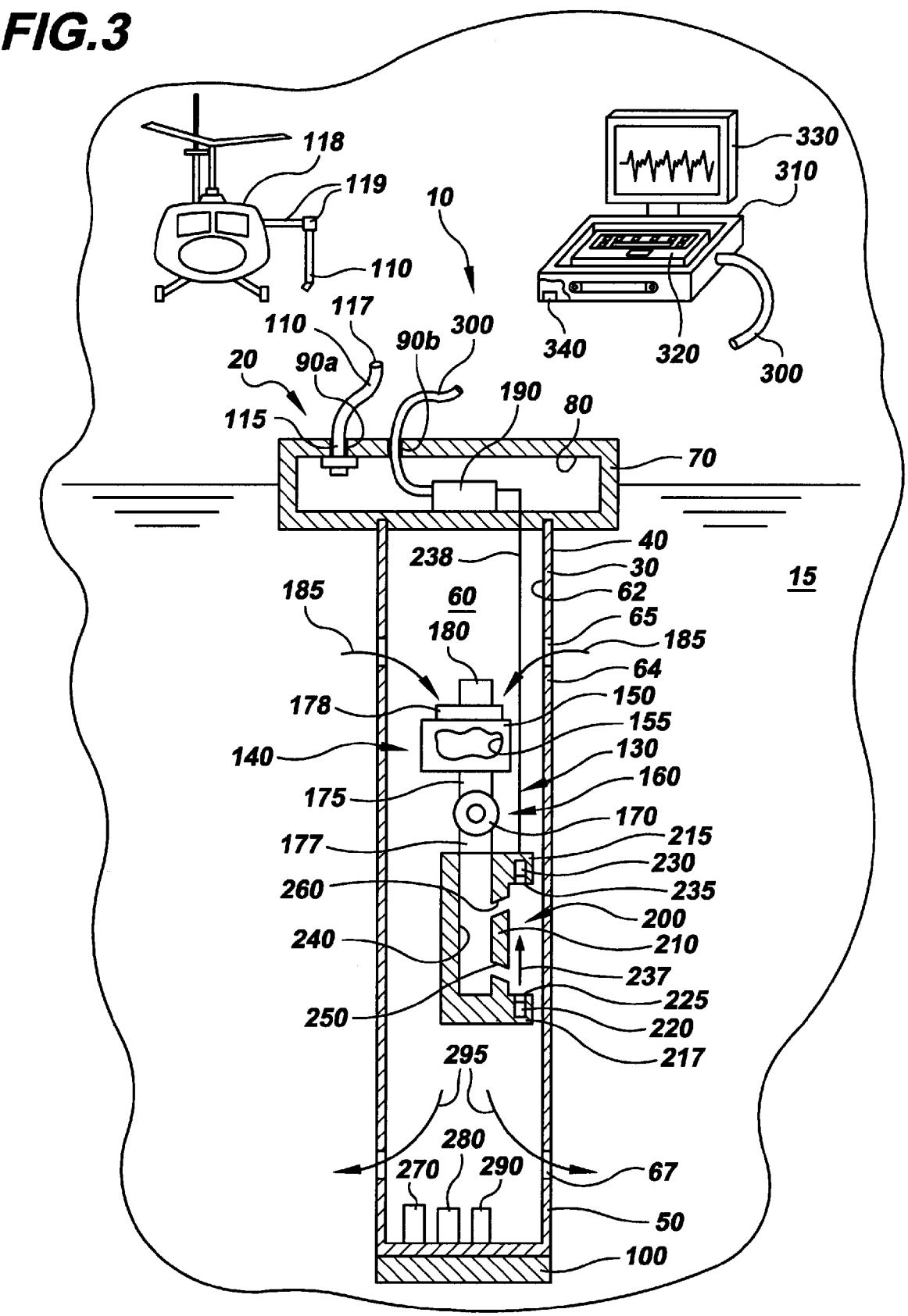
FIG. 3 is a view in partial elevation of the first embodiment portable profiler, this view showing an aerial vehicle for deploying the profiler in the marine biosphere.

As best seen in FIGS. 2 and 3, disposed in interior 60 of tubular member 30 is a test assembly, generally referred to as 130, to perform predetermined measurements of bioluminescence and other characteristics of biosphere 15. Test assembly 130 comprises a light sensitive detector assembly, generally referred to as 140, disposed in tubular member 30 between first holes 65 and second holes 67 for detecting bioluminescence. Light sensitive detector assembly 140 comprises a test chamber 150 defining a light-tight and darkened cavity 155 therein for receipt of water in which bioluminescent marine organisms (not shown) may be suspended. In this regard, cavity 155 may have a volume of about 25 milliliters.

In communication with cavity 155 are an inlet opening (not shown) and an outlet opening (also not shown) for allowing ingress and egress, respectively, of water into and out of cavity 155. In this regard, coupled to the outlet opening of cavity 155 is a pump assembly, generally referred to as 160, for suctioning the water through cavity 155. Pump assembly 160 comprises an electric pump 170 having a suction end 175 coupled to the outlet opening of cavity 155. Pump 170 is in fluid communication with the water in cavity 155 for suctioning the water through cavity 155. Pump 170 also has an outlet end 177 for reasons described hereinbelow. Disposed at the inlet opening of cavity 155 is a mesh filter 178 for filtering debris from the water entering cavity 155. Filtering debris from the water enhances accuracy, reliability and validity of test results obtained from cavity 155. Mounted atop filter 178 and in communication with cavity 155 is a light-sensitive sensor, such as a photodetector 180, for sensing light emitted by bioluminescent marine organisms in cavity 155. In this regard, photodetector 180 may be a one-inch diameter photodetector tube available from Hamamatsu Photonics, K.K., located in Hamamatsu City, Japan.

Referring again to FIGS. 2 and 3, pump 170 suctions water, including any bioluminescent organisms therein, through inlet port 65 and along first flow path 185. The water then flows through filter 178 and into cavity 155 for detection of bioluminescence that may be emitted therein. By way of example only, and not by way of limitation, pump 170 may suction water through cavity 155 at a constant rate of about 0.25 liters per second, so that test results do not vary due to a varying flow rate. As the water enters cavity 155, any living and healthy bioluminescent organisms therein will emit light detectable by photodetector 180. It may be appreciated that bioluminescence of the marine organisms present in cavity 155 is caused either by the organisms impacting mesh filter 178 or by turbulent motion of the water passing through cavity 155. Turbulence associated with water mixing in cavity 155 stimulates bioluminescent plankton (i.e., single-cell dinoflagellates) to emit light within the darkened cavity 155 and in front of photodetector 180. Also, as water is suctioned through cavity 155, small bioluminescent zooplankton may also be sampled and contribute to the overall bioluminescent signal. In response to any bioluminescence, photodetector 180 will then generate an output signal that travels to an electronics unit 190 such as by means of an electrical conduit (not shown), for purposes described more fully hereinbelow. Electronics unit 190 is disposed in chamber 80 that is defined by cap 70.

Referring yet again to FIGS. 2 and 3, profiler 10 is also capable of detecting water clarity or opaqueness. It is desirable to detect water clarity or opaqueness because detection of water clarity or opaqueness may, for example, indicate ocean regions where plankton is concentrated. It is desirable to detect a decrease in water clarity or opaqueness because dense concentrations of plankton (e.g., "red tides") may decrease water quality. Identifying such ocean regions aids environmental research projects, such as investigating variation of plankton populations over time (e.g., years).

Therefore, still referring to FIGS. 2 and 3, disposed in tubular member 30 is a transmissometer assembly, generally referred to as 200 for detecting water clarity or opaqueness. Transmissometer assembly 200 is in fluid communication with biosphere 15 via ports 65. Transmissometer assembly 200 comprises a generally elongate body 210 having a first leg portion 215 and a second leg portion 217 outwardly projecting therefrom. Mounted in second leg portion 217, but in optical communication with the water in interior 60, is an LED (Light Emitting Diode) 220. LED 220 is connected to electronics unit 190 by means of an electrical conduit (not shown) that supplies electrical power to LED 220. LED 220 is sealingly covered by a first window 225 for protecting LED 220 from corrosive attack of water and debris present in interior 60. By way of example only, and not by way of limitation, LED 220 may emit a monochromatic red light signal having a wavelength between approximately 620 nanometers and 690 nanometers. A contemplated wave length is approximately 680 nanometers. An LED suitable for this purpose is available from Wet Labs, Incorporated located in Philomath, Oreg., U.S.A.

Referring again to FIGS. 2 and 3, transmissometer assembly 200 further comprises a light detector 230 that is aligned with LED 220 and in optical communication therewith. Light detector 230 is sealingly covered by a second window 235 for protecting light detector 230 from corrosive attack of water and debris present in interior 60. The amount of light from LED 220 that is detected by light detector 230 indicates water clarity or opaqueness of biosphere 15. Light emitted by LED 220 will follow a light path 237 to reach light detector 230. Light detector 230 generates a light detector output signal which is conducted by an electrical conduit 238 to electronics unit 190, for reasons provided hereinbelow. Moreover, body 210 defines a hollow portion 240 therein that is in fluid communication with the previously mentioned outlet end 177 of pump 170. Formed in body 210 and in communication with hollow portion 240 is a first channel 250 angled with respect to first window 225. Also formed in body 210 and in communication with hollow portion 240 is a second channel 260 angled with respect to second window 235. In this regard, it may be understood from the description immediately hereinabove that as pump 170 suctions water through cavity 155 and into hollow portion 240, the water will flow through first channel 250 and second channel 260 to impinge first window 225 and second window 235, respectively. As the water impinges first window 225 and second window 235, the water will tend to wash windows 225 and 235 clear of corrosive particles and debris. It is important to wash windows 225 and 235, so that windows 225 and 235 are free of corrosive particles and debris that might otherwise block transmission of light from LED 220 or receipt of light by light detector 230. In other words, it is important that the light signal 237 emitted by LED 220 is received by light detector 230 in order to measure clarity of water residing therebetween. Therefore, presence of corrosive particles and debris on either first window 225 or second window 235 interferes with such measurements.

Again referring to FIGS. 2 and 3, a temperature thermister 270 is disposed in interior 60 of tubular member 30, and is in fluid communication with biosphere 15 via ports 65, for measuring temperature in biosphere 15 by measuring the water temperature within interior 60. Also disposed in interior 60 and in fluid communication with biosphere 15 via ports 65 is a conductivity (i.e., salinity) detector 280 for measuring electrical conductivity (i.e., salinity) of the biosphere 15 by measuring electrical conductivity of the water within interior 60. Further, disposed in interior 60, and in fluid communication with biosphere 15 via ports 65, is a depth detector 290 for measuring depth of housing 20 in biosphere 15 by measuring water pressure or hydraulic head in interior 60. In this manner, light-sensitive detector assembly 140, thermister 270, conductivity detector 280 and depth detector 290 profiles biosphere 15 as these components take measurements in biosphere 15. Moreover, each of light-sensitive detector assembly 140, thermister 270, conductivity detector 280 and depth detector 290 is connected to electronics unit 190, such as by respective ones of a plurality of electrical conduits (not shown), for reasons described hereinbelow.

Still referring to FIGS. 2 and 3, it may be appreciated that, as pump 170 operates, water is suctioned through inlet ports 65 and along flow paths 185. The water then flows through mesh filter 178 which blocks debris from entering cavity 155. As the water flows from cavity 155 and through pump 170, the water enters hollow portion 240 of body 210. As the water enters hollow portion 240, the water flows through first channel 250 and second channel 260. Water flowing through first channel 250 and second channel 260 impinges first window 225 and second window 235 respectively for washing windows 225 and 235. Moreover, as water washes windows 225 and 235, the water flows toward outlet ports 67 and then exits therethrough generally along second flow paths 295. Also, it may be appreciated that, as housing 20 is deployed in the lake, stream, river or ocean, interior 60 fills with water. In this manner, cavity 155, pump 170, led 220, light detector 215, thermister 270, salinity detector 280 and depth detector 290 are immersed in biosphere 15, via water intake through ports 67 and 65, for proper measurements in biosphere 15.

Referring again to FIG. 2, electronics unit 190 is capable of receiving electrical output signals from photodetector 180, light detector 230, thermister 270, salinity detector 280 and depth detector 290. The output signals generated by the afore mentioned components are thereafter ultimately transmitted to a data transmission cable 300, which has one end thereof connected to electronics unit 190 and the other end connected to a processor 310, which may be a data analysis and storage device, such as a portable laptop computer. For example, an electrical conduit (not shown) interconnects photodetector 180 to electronics unit 190, so that output signals of the afore-mentioned components are ultimately transmitted to data transmission cable 300. Laptop computer 310 may be disposed aboard deployment vessel 120. Laptop computer 310 is capable of receiving, automatically analyzing and processing the electrical output pulses transmitted along data transmission cable 300 and then storing the electrical output pulses. In this regard, laptop computer 310 includes a keyboard 320 for entering input data into laptop computer 310, a display monitor 330 and a data storage medium 340, such as a computer "hard disk", for random access memory storage and/or read only memory storage of the data and analysis performed using the data. Data storage medium 340 is integrally coupled to laptop computer 310. Analysis of the data received by laptop computer 310 may be by means of a suitable computer analysis software program residing in memory in laptop computer 310. The data being transmitted along data transmission cable 300 and received by laptop computer 310 may be displayed on display monitor 330 for real-time visual analysis. In addition, display monitor 330 is capable of displaying results of analyses performed by the data analysis computer software program stored in laptop computer 310. Displaying results of the analyses on display monitor 330 aids the operator of profiler 10 in immediately observing trends in the data. It may be appreciated that laptop computer 310, which is disposed aboard deployment vessel 120 or helicopter 118, is capable of supplying power to photodetector 180, light detector 230, thermister 270, salinity detector 280 and depth detector 290 by means of data transmission cable 300 in addition to receiving data (i.e., detector data) from these components by means of data transmission cable 300.

Figure 4:
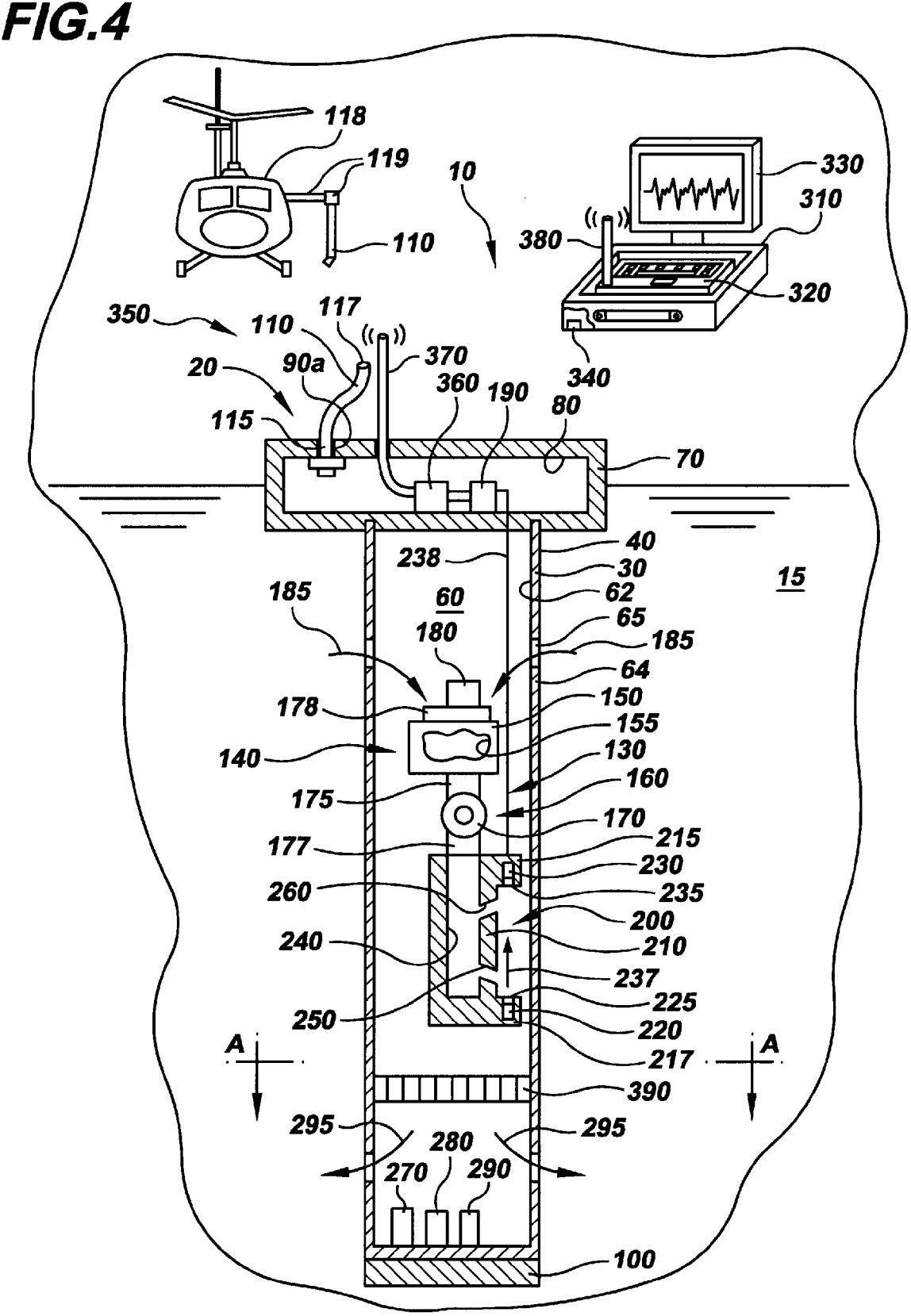
FIG. 4 is a view in partial elevation of a second embodiment portable profiler, this view showing a radio frequency transmitter for broadcasting a data signal to the laptop computer disposed aboard the aerial vehicle.
Figure 5:
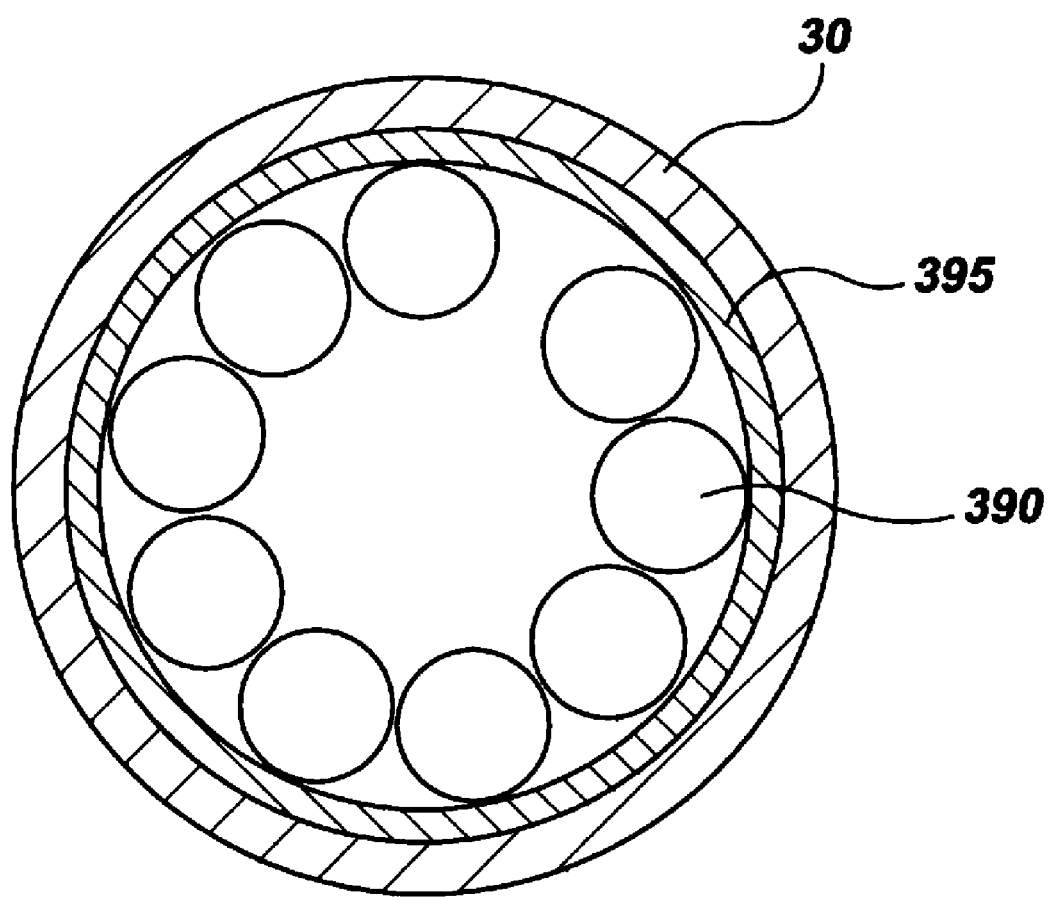
FIG. 5 is a view along section line A-A of FIG. 4.

Turning now to FIGS. 4 and 5, there is shown a second embodiment portable profiler, generally referred to as 350. Second embodiment profiler 350 comprises an RF (Radio Frequency) transmitter 360 integrally connected to electronics unit 190. By means of electronics unit 190, transmitter 360 receives data from photodetector 180, light detector 230, thermister 270, salinity detector 280 and depth detector 290. Connected to transmitter 360 and extending through second bore 90b is a first antenna 370 for broadcasting profiler data to laptop computer 310, which has a second antenna 380 integrally connected thereto for receiving the broadcast data from first antenna 370.

Still referring to FIGS. 4 and 5, disposed in interior 60 of tubular member 30 may be a water-proofed battery arrangement comprising a plurality of batteries 390 removably coupled to inner wall 62 of tubular member 30. In this regard, each of batteries 390 may reside in respective ones of a plurality of pockets (not shown) defined by a battery belt 395 that is connected to inner wall 62. Batteries allow operation of profiler 350 without need for data transmission cable 300 that would otherwise power components of profiler 350 and transmit data from profiler 350. Thus, this second embodiment provides a convenient means of operating profiler 10 without use of cable 300. In addition, it may be appreciated from the description hereinabove that batteries 390 do not provide alternating current (AC). Hence, batteries 390 may be rechargeable, if desired, because batteries 390 do not provide AC power. Rather, batteries 390 provide direct current (DC) power.

Figure 6:
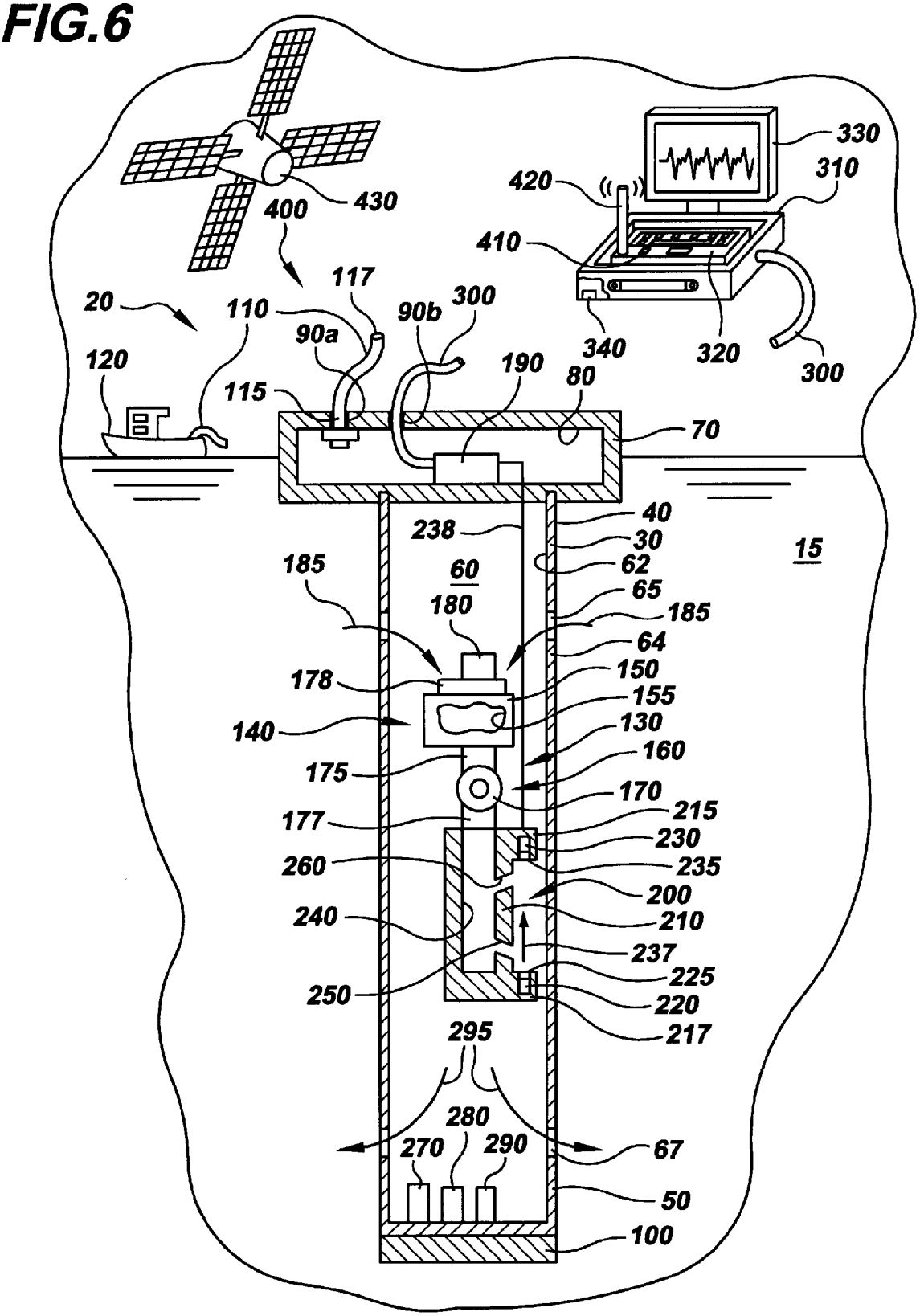
FIG. 6 is a view in partial elevation of a third embodiment portable profiler, this view showing a radio frequency transmitter for broadcasting the data signal to the laptop computer that in turn transmits the data signal to an overhead satellite.

As best seen in FIG. 6, there is shown a third embodiment profiler, generally referred to as 400. Third embodiment profiler 400 comprises an RF radio transmitter 410 including the second antenna 420 for broadcasting a data signal to an overhead satellite 430. Overhead satellite 430, in turn, relays the data signal to an internet network (not shown) for retrieval and further analysis. Satellite 430 may be in near polar orbit, sun synchronous orbit or geosynchronous orbit, as required by the location of profiler 400.

Figure 7:
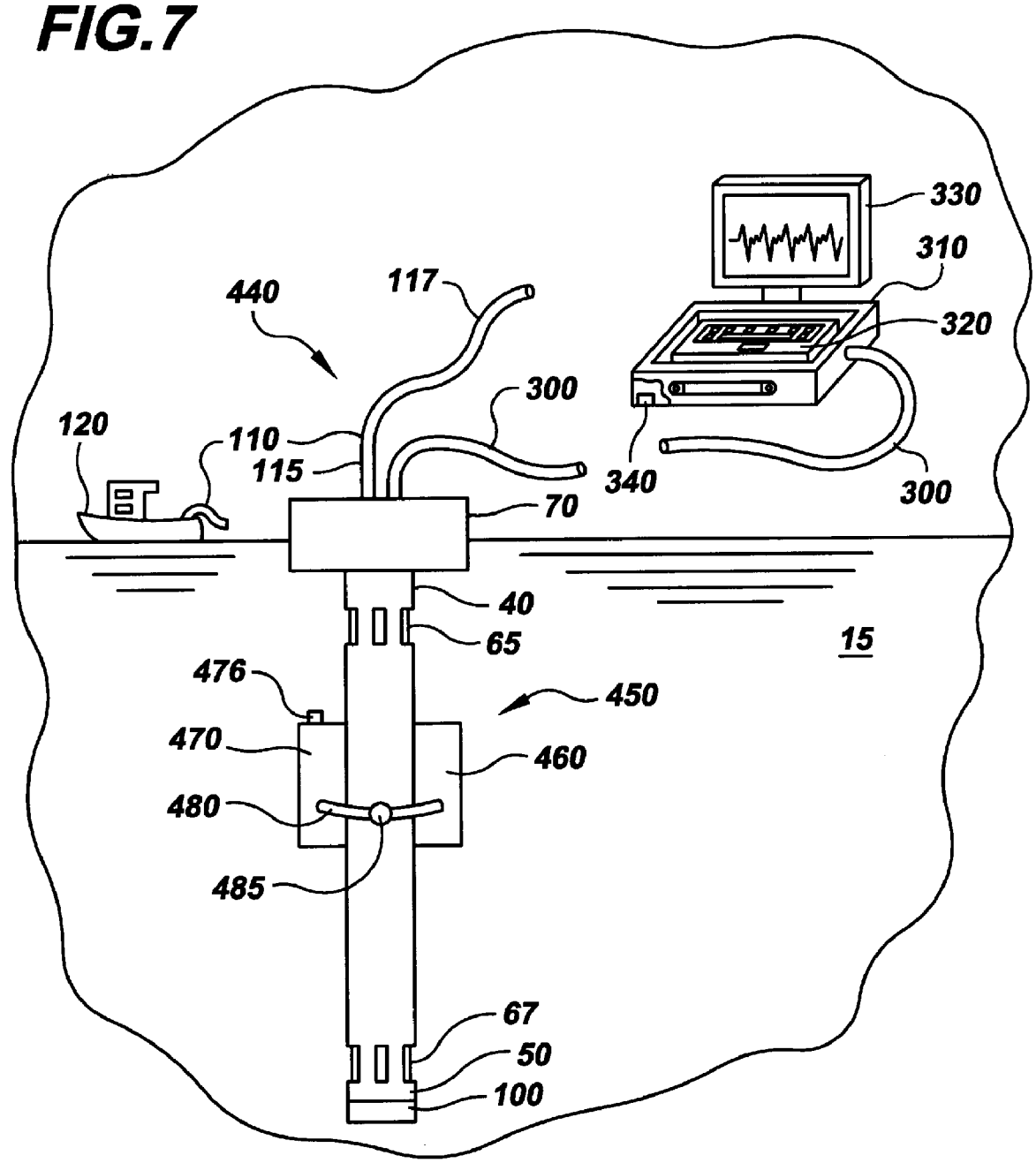
FIG. 7 is a view in elevation of a fourth embodiment portable profiler, this view showing an adjustable ballast for vertical descent and assent of the profiler in the marine biosphere.
Figure 8:
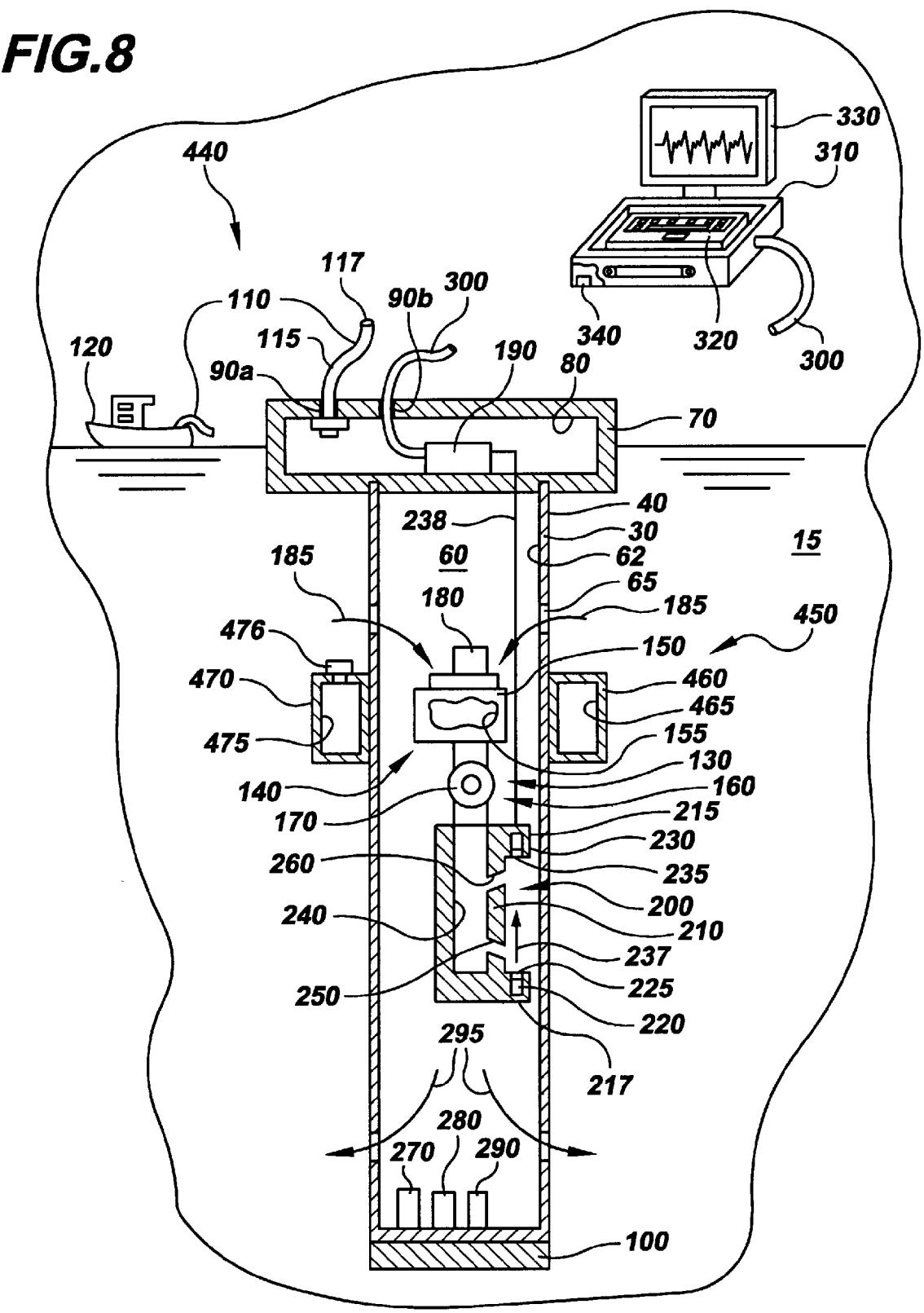
FIG. 8 is a view in elevation of the fourth embodiment portable profiler.

Referring to FIGS. 7 and 8, a fourth embodiment portable profiler, generally referred to as 440, includes an adjustable ballast generally referred to as 450 for causing housing 20 to vertically descend and ascend in biosphere 15. Adjustable ballast 450 thereby controls buoyancy of profiler 440 while disposed in biosphere 15. Ballast 450 comprises a first ballast tank 460 coupled to outer wall 64 as shown in FIG. 1, of tubular member 30. First ballast tank 460 defines a leak-tight first chamber 465 therein. Also coupled to outer wall 64 of tubular member 30 is a second ballast tank 470. Second ballast tank 470 also defines a leak-tight second chamber 475 therein and includes an electrically operable pressure release valve 476 in communication with second chamber 475. Interconnecting first chamber 465 and second chamber 475 is a conduit 480 having an electrically operable flow valve 485 disposed therein, for reasons disclosed herein below.

Still referring to FIGS. 7 and 8, prior to deployment of portable profiler 440, first chamber 465 is filled with a predetermined amount of pressurized gas, such as air. During deployment of profiler 440 in biosphere 15, housing 20 is caused to vertically descend to a predetermined depth in biosphere 15 for testing characteristics (e.g., presence of bioluminescent organisms) of biosphere 15 at the predetermined depth. When deployed in biosphere 15, profiler 440 will tend to sink, due in part to the relatively dense gas in first ballast tank 460 and ballast member 100, if present. However, the amount of descent of profiler 440 is controlled by operating flow valve 485, which causes a metered release of gas from first ballast tank 460, through conduit 480 and into second ballast tank 470. As the gas enters empty second ballast tank 470, the gas will tend to expand to add buoyancy to profiler 440 and slow or stop vertical descent of profiler into biosphere 15. Pressure release valve 476 may be operated during this time for releasing the gas in second ballast tank 470 to add more buoyancy to profiler 440. In other words, expansion of gas in second ballast tank 470 and release of gas in second ballast tank 470 will cause housing 20 to vertically rise in biosphere 15. In this manner housing 20 has an adjustably buoyancy. Operation of adjustable ballast 450 is controlled by laptop computer 310 in cooperation with electronics unit 190. Electronics unit 190 is coupled to release valve 476 and flow valve 485 for controlling operation of release valve 476 and flow valve 485.

Figure 9:
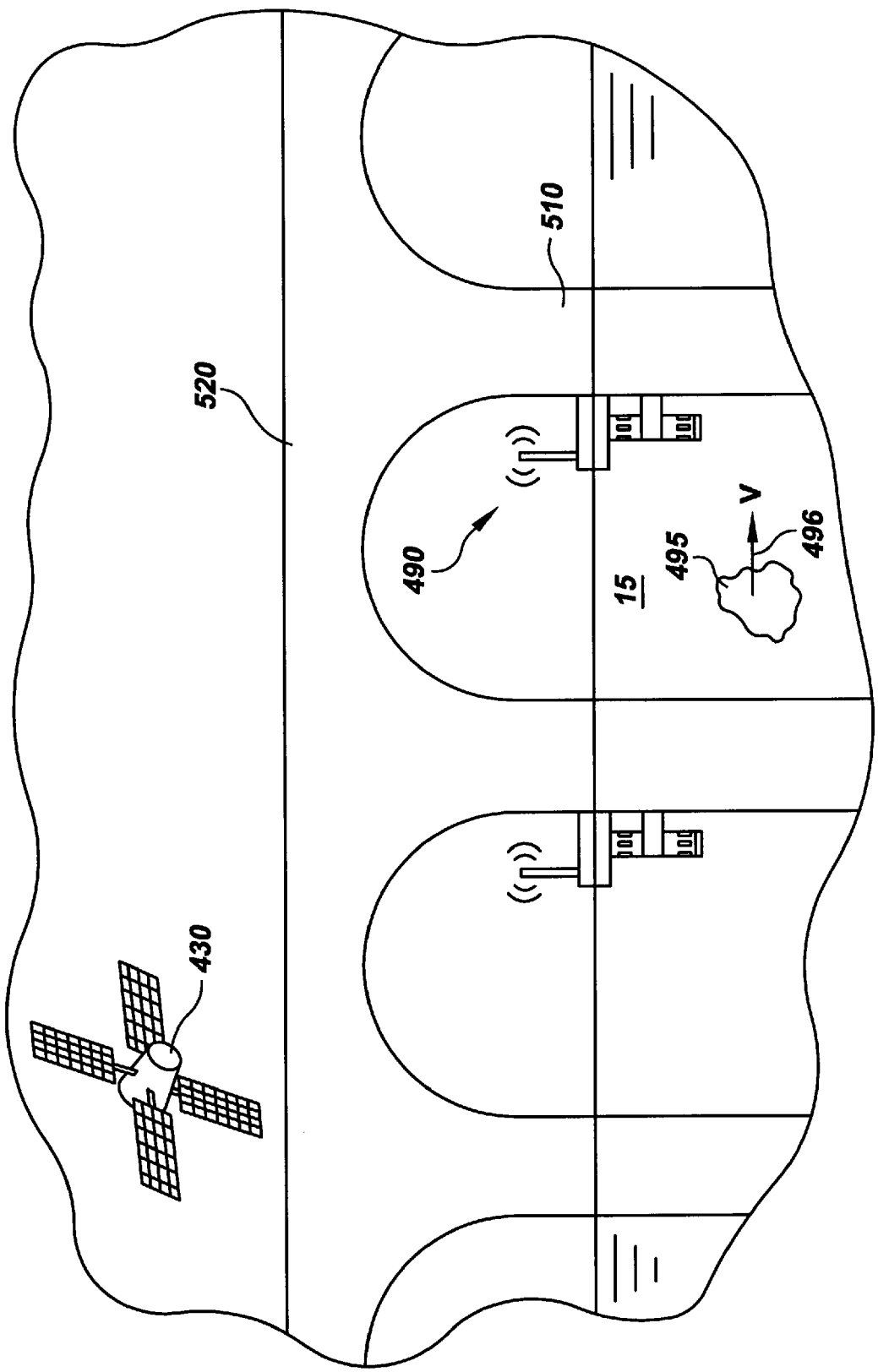
FIG. 9 is a view in elevation of a fifth embodiment portable profiler for detecting the presence of objects, such as seagoing vehicles, in the marine biosphere.

Referring to FIG. 9, there is shown a fifth embodiment portable profiler, generally referred to as 490, for detecting unauthorized presence of an object 495 traveling at a velocity "V" along a velocity vector 496. With regard to this fifth embodiment of the portable profiler, housing 20 is removably connected to a structure near biosphere 15, such as a support column 510 of a bridge 520 that may span biosphere 15. Housing 20 is removably connected to support column 510, so that housing 20 may be removed from support column 510 and relocated (i.e., ported) and connected to a different structure (e.g., a pier). This fifth embodiment profiler 490 is similar to second embodiment profiler 350, except cable 117 is not needed for deployment because fifth embodiment is removably connected to column 510. As object 495 moves through biosphere 15, the object 495 will generate turbulence in biosphere 15. Such turbulence will, in turn, cause bioluminescent organisms residing in biosphere 15 to luminescence. Such organisms will be detected by firth embodiment profiler 490, which will in turn broadcast detector data to satellite 430. Satellite 430 will, in turn, transmit the data to a remote receiver (e.g., a remote Internet website) for analysis.

By way of example only, and not by way of limitation, during operation of profilers 10, 350, 400 or 440, photodetector 180 is powered-up for about four seconds before pump 170 is activated for about 10 seconds. During the 10 second sampling period, bioluminescence is quantified and averaged. As pump 170 is deactivated, percent transmission of water clarity is measured. The raw data are then sent, for example via data transmission cable 300, to laptop computer 310 that logs the data into data storage medium 340. The data are then processed automatically and can be posted to a tealtime web address via RF or satellite link, as previously mentioned.

While the invention has been described with particular reference to its representative embodiments, it will be understood by those skilled in the art that various changes may be made and equivalents may be substituted for elements of the representative embodiments without departing from the invention. For example, batteries 390 may be recharged by means of solar panels (not shown) electrically coupled thereto for receiving solar energy, so that retrieval of profiler 350 from biosphere 15 merely to recharge or replace batteries 390 is unnecessary. As another example, a suitable camera (also not shown) may be mounted on tubular member 30 for visually recording events in the biosphere, such as presence of objects that may be the cause of bioluminescent activity. As yet another example, any of the various embodiments of the profiler described herein may be untethered from deployment vessel 120 or helicopter 118 and thereby allowed to drift (with a suitable flotation collar integrally attached thereto) with any current present in the marine biosphere. In this case, satellite 430 will receive broadcast data from the profiler and also track the profiler's location as the profiler drifts in biosphere 15.

Therefore, what is provided is a portable profiler for profiling a marine biosphere and method of assembling the profiler.

What is claimed is:

1. A portable profiler for profiling a marine biosphere, comprising:
   a housing;
   a ballast coupled to said housing for controlling movement of said housing in the biosphere;
   a light-sensitive detector assembly coupled to said housing for detecting bioluminescence, said detector assembly capable of generating an output signal in response to the bioluminescence detected thereby; and
   a data analysis and storage device coupled to said light-sensitive detector assembly for receiving the output signal.

2. The portable profiler of claim 1, wherein said ballast is an adjustable ballast for adjusting depth of said housing in the biosphere.

3. The portable profiler of claim 1, wherein said adjustable ballast is a gas operable adjustable ballast.

4. The portable profiler of claim 1, wherein said adjustable ballast is configured to control the buoyancy of said housing in the biosphere.

5. The portable profiler of claim 1, further comprising a transmissometer assembly coupled to said housing for detecting opaqueness of the biosphere.

6. The portable profiler of claim 1, further comprising a thermister coupled to said housing for measuring temperature of the biosphere.

7. The portable profiler of claim 1, further comprising a salinity detector coupled to said housing for measuring salinity of the biosphere.

8. The portable profiler of claim 1, further comprising a depth detector coupled to said housing for detecting depth of said housing in the biosphere.

9. The portable profiler of claim 1, further comprising a radio frequency transmitter coupled to said light-sensitive detector for broadcasting the output signal.

10. The portable profiler of claim 9, wherein said radio frequency transmitter is capable of broadcasting the output signal to said data analysis and storage device.

11. The portable profiler of claim 9, wherein said radio frequency transmitter is capable of broadcasting the output signal to a satellite.

12. The portable profiler of claim 1, further comprising a battery coupled to said light-sensitive detector assembly for powering said light-sensitive detector assembly.

13. A portable profiler for profiling a marine biosphere, comprising:
   a housing, wherein said housing is man-portable;
   a ballast coupled to said housing for controlling movement of said housing in the biosphere, said ballast being an adjustable ballast for adjusting dept of said housing in the biosphere;
   a light-sensitive detector assembly coupled to said housing for detecting bioluminescence, said detector assembly configured to generate an output signal in response to the bioluminescence detected thereby;
   a data analysis and storage device coupled to said light-sensitive detector assembly for receiving the output signal; and
   a storage medium coupled to said data analysis and storage device for storing the output signal.

14. The portable profiler of claim 13, further comprising:
   a transmissometer assembly coupled to said housing for detecting opaqueness of the biosphere;
   a thermister coupled to said housing for measuring temperature of the biosphere;
   a salinity detector coupled to said housing for measuring salinity of the biosphere; and
   a depth detector coupled to said housing for detecting depth of said housing in the biosphere.

15. A portable profiler for profiling a marine biosphere, comprising:
   a housing, wherein said housing is low-weight for portability;
   an adjustable ballast coupled to said housing for controlling movement of said housing in the biosphere, said adjustable ballast including:
      a first tank capable of having pressurized gas therein;
      a second tank capable of receiving the pressurized gas, said second tank disposed near said first tank;
      a conduit interconnecting said first tank and said second tank; and
      a flow valve coupled to said conduit for controlling flow of the gas between said first tank and said second tank;
   a light-sensitive detector assembly coupled to said housing for detecting bioluminescence, said detector assembly capable of generating an output signal in response to the bioluminescence detected thereby; and
   a data analysis and storage device coupled to said light-sensitive detector assembly for receiving the output signal.

16. The profiler of claim 15, wherein said adjustable ballast is configured to control the buoyancy of said housing in the biosphere.

17. The portable profiler of claim 15, further comprising:
   a transmissometer assembly coupled to said housing for detecting opaqueness of the biosphere;
   a thermister coupled to said housing for measuring temperature of the biosphere;
   a salinity detector coupled to said housing for measuring salinity of the biosphere; and
   a depth detector coupled to said housing for detecting depth of said housing in the biosphere.

18. The portable profiler of claim 15, further comprising a radio frequency transmitter coupled to said light-sensitive detector for broadcasting the output signal, said transmitter including an antenna for strengthening the broadcast.

19. The portable profiler of claim 18, wherein said radio frequency transmitter is capable of broadcasting the output signal to said data analysis and storage device.

20. The portable profiler of claim 18, wherein said radio frequency transmitter is configured to broadcast the output signal to a satellite.

21. The portable profiler of claim 15, further comprising a battery coupled to said light-sensitive detector assembly for powering said light-sensitive detector assembly.

22. A method of assembling a portable profiler for profiling a marine biosphere, comprising the steps of:
   (a) providing a housing;
   (b) coupling a ballast to the housing for controlling movement of the housing in the biosphere;
   (c) coupling a light-sensitive detector assembly to the housing for detecting bioluminescence, the detector assembly configured to generate an output signal in response to the bioluminescence detected thereby; and
   (d) coupling a data analysis and storage device to the light-sensitive detector assembly for receiving the output signal.

23. The method of claim 22, wherein the step of coupling a ballast to the housing comprises the step of coupling an adjustable ballast to the housing for adjusting depth of the housing in the biosphere.

24. The method of claim 23, wherein the step of coupling an adjustable ballast to the housing comprises the step of coupling a gas operable adjustable ballast to the housing.

25. The method of claim 22, wherein the step of coupling a ballast to the housing comprises the step of coupling the ballast so that the ballast is configured to control the buoyancy of the housing.

26. The method of claim 22, further comprising the step of coupling a transmissometer assembly to the housing for detecting opaqueness of the biosphere.

27. The method of claim 22, further comprising the step of coupling a thermister to the housing for measuring temperature of the biosphere.

28. The method of claim 22, further comprising the step of coupling a salinity detector to the housing for measuring salinity of the biosphere.

29. The method of claim 22, further comprising the step of coupling a depth detector to the housing for detecting depth of the housing in the biosphere.

30. The method of claim 22, further comprising the step of coupling a radio frequency transmitter to the light-sensitive detector for broadcasting the output signal.

31. The method of claim 30, wherein the step of coupling a radio frequency transmitter to the light-sensitive detector comprises the step of coupling a radio frequency transmitter configured to broadcast the output signal to the data analysis and storage device.

32. The method of claim 30, wherein the step of coupling a radio frequency transmitter to the light-sensitive detector comprises the step of coupling a radio frequency transmitter configured to broadcast the output signal to a satellite.

33. The method of claim 22, further comprising the step of coupling a battery to the light-sensitive detector assembly for powering the light-sensitive detector assembly.

34. A method of assembling a portable profiler for profiling a marine biosphere, comprising the steps of:
   (a) providing a housing, wherein the housing is low-weight for portability;
   (b) coupling a ballast to the housing for controlling movement of the housing in the biosphere, wherein the step of coupling a ballast to the housing includes the step of coupling an adjustable ballast to the housing for adjusting depth of the housing in the biosphere;
   (c) coupling a light-sensitive detector assembly to the housing for detecting bioluminescence, wherein the step of coupling a light-sensitive detector assembly to the housing includes the step of coupling a light-sensitive detector assembly configured to generate an output signal in response to the bioluminescence detected thereby;
   (d) coupling a data analysis and storage device to the light-sensitive detector assembly for receiving the output signal.

35. The method of claim 34, wherein the step of coupling an adjustable ballast to the housing comprises the step of coupling the adjustable ballast so that the adjustable ballast is configured to control the buoyancy of the housing.

36. The method of claim 34, further comprising:
   (a) coupling a transmissometer assembly to the housing for detecting opaqueness of the biosphere;
   (b) coupling a thermister to the housing for measuring temperature of the biosphere
   (c) coupling a salinity detector to the housing for measuring salinity of the biosphere; and
   (d) coupling a depth detector to the housing for detecting depth of the housing in the biosphere.

37. A method of assembling a portable profiler for profiling a marine biosphere, comprising the steps of:
   (a) providing a housing, wherein the housing is man-portable;
   (b) coupling an adjustable ballast to the housing for controlling movement of the housing in the biosphere, the adjustable ballast including:
      (i) a first tank capable of having pressurized gas therein;
      (ii) a second tank configured to receive the pressurized gas, the second tank disposed near the first tank;
      (iii) a conduit interconnecting the first tank and the second tank; and
      (iv) a flow valve coupled to the conduit for controlling flow of the gas between the first tank and the second tank;
   (c) coupling a light-sensitive detector assembly to the housing for detecting bioluminescence, the detector assembly configured to generate an output signal in response to the bioluminescence detected thereby;
   (d) coupling a data analysis and storage device to the light-sensitive detector assembly for receiving the output signal; and
   (e) coupling a storage medium to the data analysis and storage device for storing the output signal.

38. The method of claim 35, further comprising the steps of:
   (a) coupling a transmissometer assembly to the housing for detecting opaqueness of the biosphere;
   (b) coupling a thermister to the housing for measuring temperature of the biosphere;
   (c) coupling a salinity detector to the housing for measuring salinity of the biosphere; and
   (d) coupling a depth detector to the housing for detecting depth of the housing in the biosphere.

39. The method of claim 35, further comprising the step of coupling a radio frequency transmitter to the light-sensitive detector for broadcasting the output signal, the transmitter including an antenna for strengthening the broadcast.

40. The method of claim 37, wherein the step of coupling a radio frequency transmitter to the light-sensitive detector comprises the step of coupling a radio frequency transmitter configured to broadcast the output signal to the data analysis and storage device.

41. The method of claim 37, wherein the step of coupling a radio frequency transmitter to the light-sensitive detector comprises the step of coupling a radio frequency transmitter configured to broadcast the output signal to a satellite.

42. The method of claim 35, further comprising the step of coupling a battery to the light-sensitive detector assembly for powering the light-sensitive detector assembly.

* * * * *